United States Patent
Ntinika et al.

(10) Patent No.: US 11,185,654 B2
(45) Date of Patent: Nov. 30, 2021

(54) PRESSURIZED GAS ADAPTOR

(71) Applicants: Calvin Ntinika, Derby, KS (US);
Reinhard Lugalia, Derby, KS (US)

(72) Inventors: Calvin Ntinika, Derby, KS (US);
Reinhard Lugalia, Derby, KS (US)

( * ) Notice: Subject to any disclaimer, the term of this patent is extended or adjusted under 35 U.S.C. 154(b) by 118 days.

(21) Appl. No.: 16/256,714

(22) Filed: Jan. 24, 2019

(65) Prior Publication Data
US 2019/0224437 A1 Jul. 25, 2019

Related U.S. Application Data

(60) Provisional application No. 62/621,157, filed on Jan. 24, 2018.

(51) Int. Cl.
| | |
|---|---|
| *A61M 16/08* | (2006.01) |
| *A62B 9/04* | (2006.01) |
| *A61M 39/22* | (2006.01) |
| *A61M 16/20* | (2006.01) |
| *A61M 39/10* | (2006.01) |

(Continued)

(52) U.S. Cl.
CPC .... *A61M 16/0816* (2013.01); *A61M 16/0875* (2013.01); *A61M 16/20* (2013.01); *A61M 39/223* (2013.01); *A62B 9/04* (2013.01); *A61M 11/02* (2013.01); *A61M 11/06* (2013.01); *A61M 16/0666* (2013.01); *A61M 16/0672* (2014.02); *A61M 16/0833* (2014.02); *A61M 16/16* (2013.01); *A61M 16/201* (2014.02); *A61M 39/10* (2013.01); *A61M 2039/1027* (2013.01); *A61M 2202/0208* (2013.01)

(58) Field of Classification Search
CPC ............ A61B 1/00112; A61B 1/00119; A61B 1/00128; A61B 1/00137; A61B 1/01; A61B 1/018; A61B 1/2676; A61M 16/00; A61M 16/04; A61M 16/0463; A61M 16/06; A61M 16/0672; A61M 16/08; A61M 16/0816; A61M 16/0833; A61M 16/20; A61M 2202/0007; A61M 2202/0208; A61M 2205/3523; A61M 39/22; A61M 39/223; A61M 39/28; A61M 5/14276; A61M 5/16804; A61M 5/16813; A62B 9/02; B63C 11/18; B63C 11/2236; B63C 11/2245; F16K 27/065; F16K 5/04; F16K 5/045; Y10S 128/912; Y10T 137/86871; Y10T 137/877; Y10T 137/87877
See application file for complete search history.

(56) References Cited

U.S. PATENT DOCUMENTS

| | | | | |
|---|---|---|---|---|
| 3,995,626 | A * | 12/1976 | Pearce, Jr. | A62B 9/02 128/205.24 |
| 4,068,657 | A * | 1/1978 | Kobzan | B63C 11/2245 114/315 |
| 4,197,876 | A * | 4/1980 | Lobdell | A61M 39/223 137/625.47 |

(Continued)

*Primary Examiner* — Annette Dixon
(74) *Attorney, Agent, or Firm* — Margaret Millikin (57) ABSTRACT

The present invention is an adaptor for connecting a pressurized gas, such as an oxygen supply, to two different outlets, with each outlet connected to a different gas delivery device. Gas delivery devices include, but are not limited to a nasal cannula, a c-pap machine, a bi-pap machine, a bubbler, or a nebulizer. The adaptor is provided with a valve located within the adaptor that can be used to direct the gas from the gas supply selectively to one of the two different outlets, or alternately, to both outlets at the same time.

13 Claims, 8 Drawing Sheets

(51) Int. Cl.
*A61M 16/06* (2006.01)
*A61M 11/06* (2006.01)
*A61M 11/02* (2006.01)
*A61M 16/16* (2006.01)

(56) References Cited

U.S. PATENT DOCUMENTS

| | | | |
|---|---|---|---|
| 4,572,239 A | 2/1986 | Koch et al. | |
| 4,840,199 A * | 6/1989 | Brunt, Jr. | A62B 9/02 128/202.27 |
| 5,694,922 A | 12/1997 | Palmer | |
| 6,978,783 B2 * | 12/2005 | Svendsen | A61M 16/0463 128/207.14 |
| 7,178,524 B2 | 2/2007 | Noble | |
| 7,320,324 B2 | 1/2008 | Willeford | |
| 7,721,738 B2 * | 5/2010 | Svendsen | A61M 16/08 128/207.14 |
| 7,823,588 B2 | 11/2010 | Hansen | |
| 8,205,913 B2 * | 6/2012 | Brewer | A61M 16/0816 285/130.1 |
| 8,770,190 B2 | 7/2014 | Doherty et al. | |
| 9,155,857 B2 | 10/2015 | Lalonde | |
| 9,308,311 B2 | 4/2016 | Hallett et al. | |
| 10,485,406 B2 * | 11/2019 | Lei | A61M 16/0816 |
| 2001/0013370 A1 | 8/2001 | Loo | |
| 2002/0193751 A1 * | 12/2002 | Theeuwes | A61M 5/14276 604/248 |
| 2006/0138377 A1 | 6/2006 | McPeak et al. | |
| 2007/0119508 A1 | 5/2007 | West et al. | |
| 2008/0000472 A1 * | 1/2008 | Wall | A61M 16/20 128/202.27 |
| 2014/0076431 A1 | 3/2014 | Duncan | |
| 2014/0166015 A1 * | 6/2014 | Waggoner | A61M 16/00 128/205.24 |
| 2014/0257198 A1 | 9/2014 | Truitt et al. | |
| 2016/0213835 A1 | 7/2016 | Levy et al. | |

* cited by examiner

PRESSURIZED GAS ADAPTOR

BACKGROUND OF THE INVENTION

1. Field of the Invention

The present invention relates to an adaptor for connecting a pressurized gas supply, such as an oxygen supply, to two different outlets. The adaptor is provided with a valve located within the adaptor that can direct the gas from the gas supply selectively to one of the two different outlets, or alternately, to both outlets at the same time.

2. Description of the Related Art

For patients that are on oxygen, there is a constant problem in switching the connection from a single gas supply to various gas delivery devices. For example, in a home setting there is a need to switch the gas connection attached to the gas supply from a nasal cannula to a c-pap machine, a bi-pap machine, or to a home ventilator. In a hospital setting, there is a need to switch the gas connection attached to the gas supply from a nasal cannula to a nebulizer, a c-pap machine, a bi-pap machine, or to a bubbler that delivers humidified gas to a one of these other gas delivery devices.

Currently when there is a need to switch the gas connection on the gas supply to a different gas delivery device, the user must physically disconnect the gas delivery tubing that extends between the gas supply and the delivery device and then reconnect that gas delivery tubing so as to create a new flow path from the gas supply to a different delivery device. This procedure can be difficult and time consuming for those patients or attending nurses that are responsible for performing the procedure.

Frequent changing of the connections can result in bad connections, stretched or leaking tubing, and in some cases, complete failure to make a connection. Failure to make a good connection can be due to inadequate strength or capability of the patient who is attempting to perform the procedure, the difficulty experienced in having to perform a cumbersome task, or simply forgetfulness.

The present invention addresses this problem by allowing the switching of gas flow by the quick and easy flip of a switch without the need for disconnecting and reattaching tubing. Even a person with limited physical ability can easily manage to employ the present adaptor to switch gas flow between various gas delivery devices.

SUMMARY OF THE INVENTION

The present invention is an adaptor for connecting a pressurized gas, such as an oxygen supply, to two different outlets, with each outlet connected to a different gas delivery device. Gas delivery devices include, but are not limited to, a nasal cannula, a c-pap machine, a bi-pap machine, a bubbler, or a nebulizer. The adaptor is provided with a valve located within the adaptor that can be used to direct the gas from the gas supply selectively to one of the two different outlets, or alternately, to both outlets at the same time.

DETAILED DESCRIPTION OF THE PREFERRED EMBODIMENT

Figure 1:
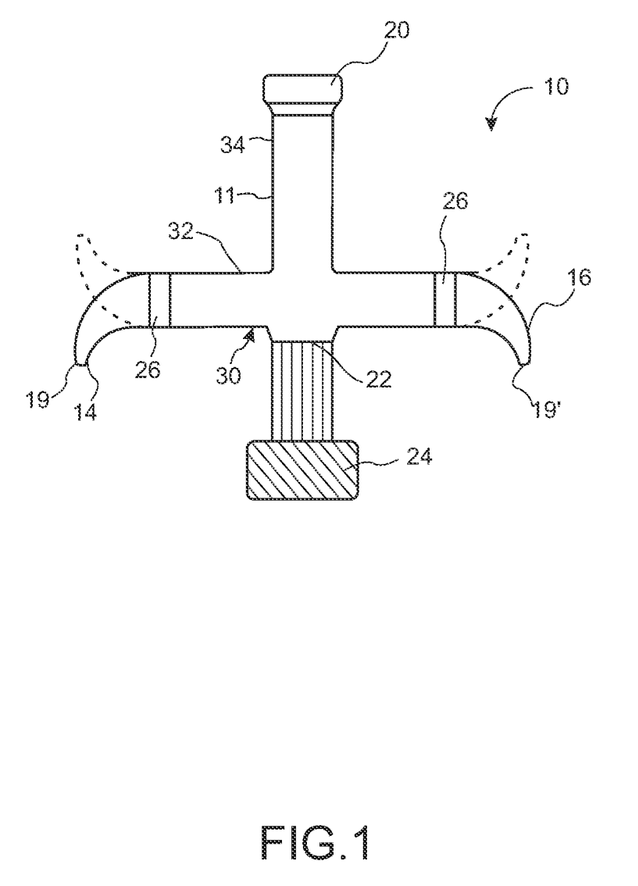
FIG. 1 is plan view of an adaptor that is constructed in accordance with a preferred embodiment of the present invention.
Figure 2:
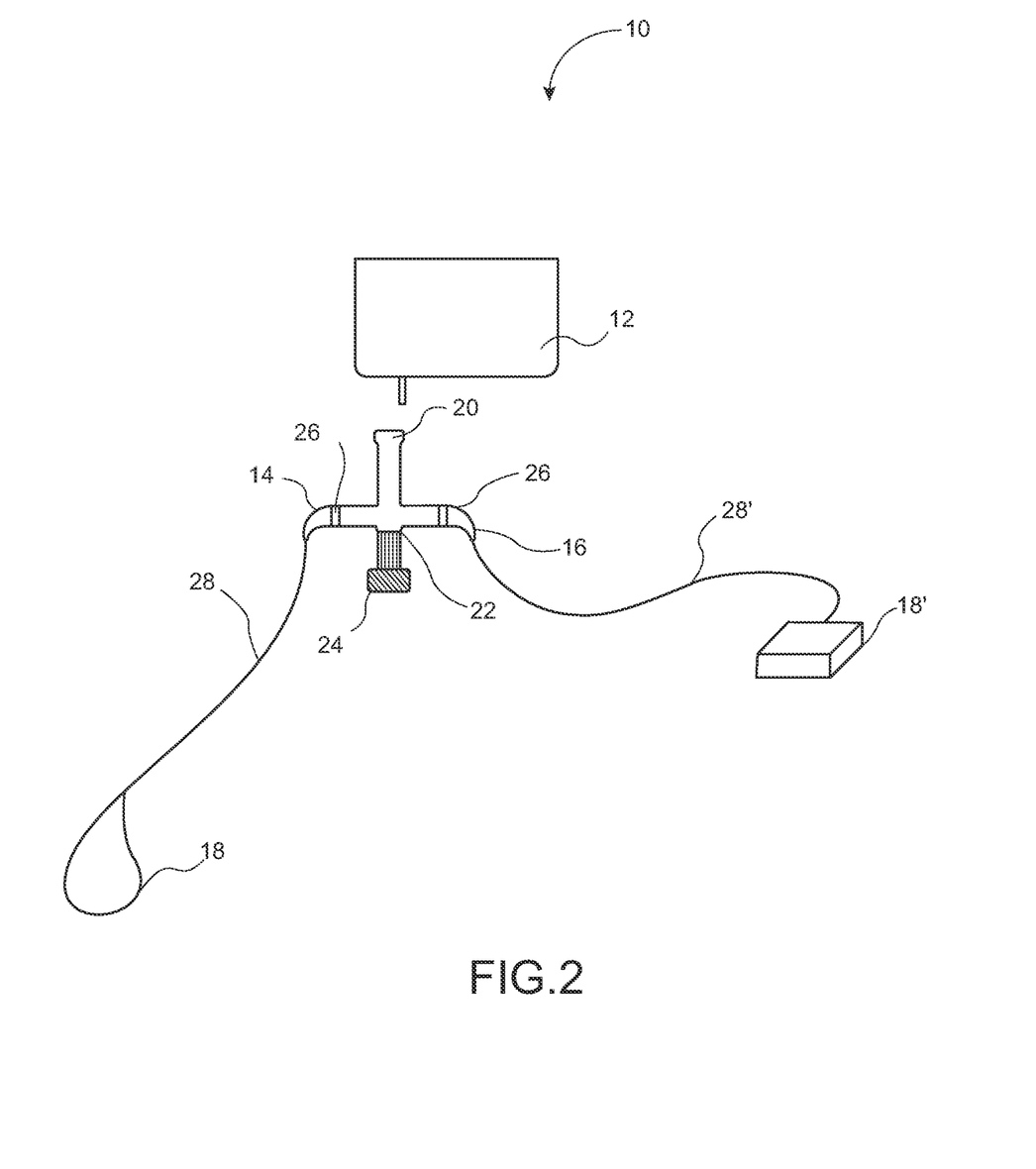
FIG. 2 is the adaptor of FIG. 1 shown in use in a typical home setting.

Referring now to FIGS. 1 and 2, there is illustrated an adaptor 10 for connecting a pressurized gas supply 12, such as an oxygen concentrator, to two different outlets 14 and 16, with each outlet 14 and 16 connected to a different gas delivery device 18 and 18'. The adaptor 10 of FIGS. 1 and 2 is generally designed for a patient's home use, although it may also be used in commercial, industrial or institutional settings.

The adaptor 10 is provided with a receiving inlet 20 that connects to a pressurized gas supply 12, such as a concentrator shown in the drawing. The adaptor 10 is hollow to allow gas to flow through it to at least two outlets 14 and 16. Positioned within the adaptor 10 is a valve 22 that is movable to various positions by a switch 24 provided on the exterior 11 of the adaptor 10 so that it can be operated by a user. The valve 22 can be moved via the switch 24 to allow gas to flow from the gas supply 12 to a first outlet 14, to a second outlet 16, or simultaneously to both the first and the second outlets 14 and 16 provided on the adaptor 10.

The outlets 14 and 16 may be curved and/or tapered toward the openings 19 and 19' in each outlet in order to securely receive, fit and/or connect tubing 28 and 28'. Associated with each of the outlets 14 and 16, the adaptor 10 is provided with a separate swivel mechanism 26 that functions to allow the outlets 14 and 16 to swivel, thereby preventing tubing 28 and 28' attached to outlets 14 and 16, respectively, from becoming twisted, tangled, or pinched.

FIG. 2 shows the adaptor 10 in a typical home installation where the first outlet 14 is connected via first tubing 28 to a nasal cannula 18 and where the second outlet 16 is connected via second tubing 28' to a c-pap machine 18'. Although the nasal cannula 18 and the c-pap machine 18' are illustrated in FIG. 2 as the gas delivery devices 18 and 18', any of a variety of gas delivery devices could alternately be attached to the first and second outlets 14 and 16. For example, some common gas delivery devices that might be attached to the outlets 14 and 16 include, but are not limited to, a nasal cannula, a c-pap machine, a bi-pap machine, a bubbler, or a nebulizer.

Figure 3:
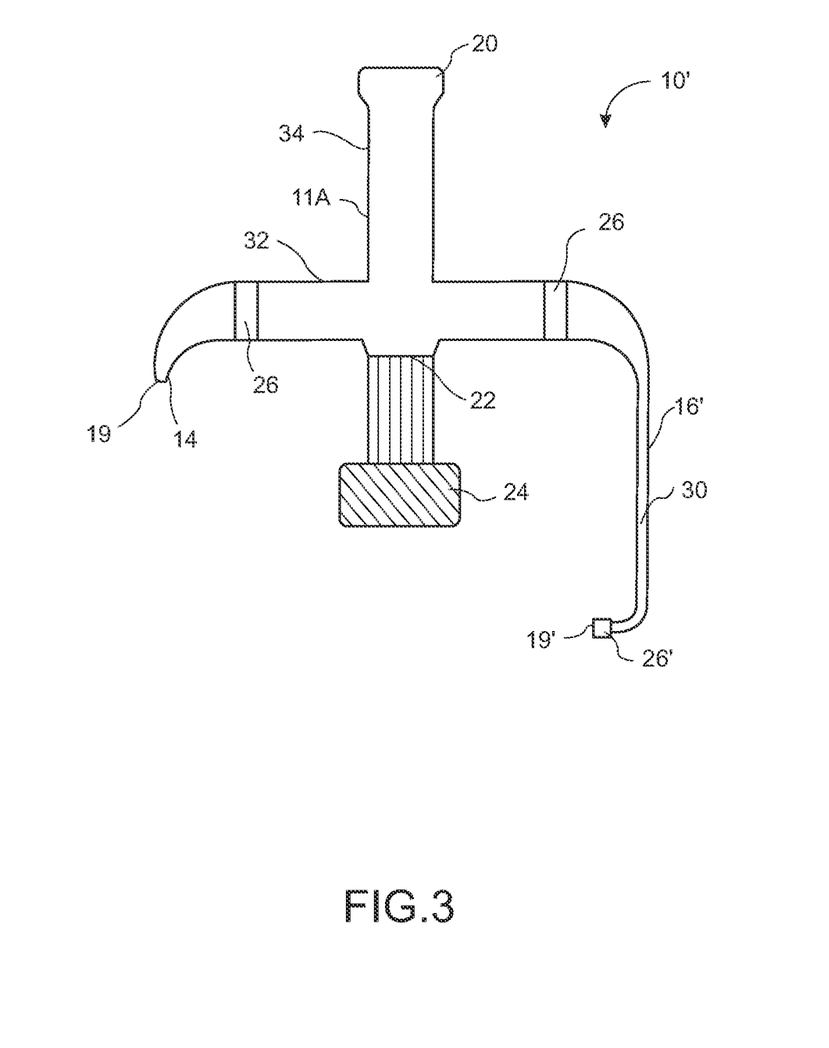
FIG. 3 is a modified adaptor of similar to the adaptor of FIG. 1 with the exception that it is provided with a modified second outlet instead of the second outlet illustrated in FIGS. 1 and 2.

Referring now to FIG. 3, there is illustrated a modified adaptor 10' which has been modified by replacing the second outlet 16 that is illustrated in FIGS. 1 and 2 with a modified second outlet 16'. The modified second outlet 16' of the modified adaptor 10' illustrated in FIG. 3 includes a flexible tube 30 that terminates with a second swivel 26'. This modified adaptor 10' is designed for attaching the modified second outlet 16' to a humidifier chamber (not illustrated) such as the bubble chamber 18A' shown in FIG. 5.

Figure 4:
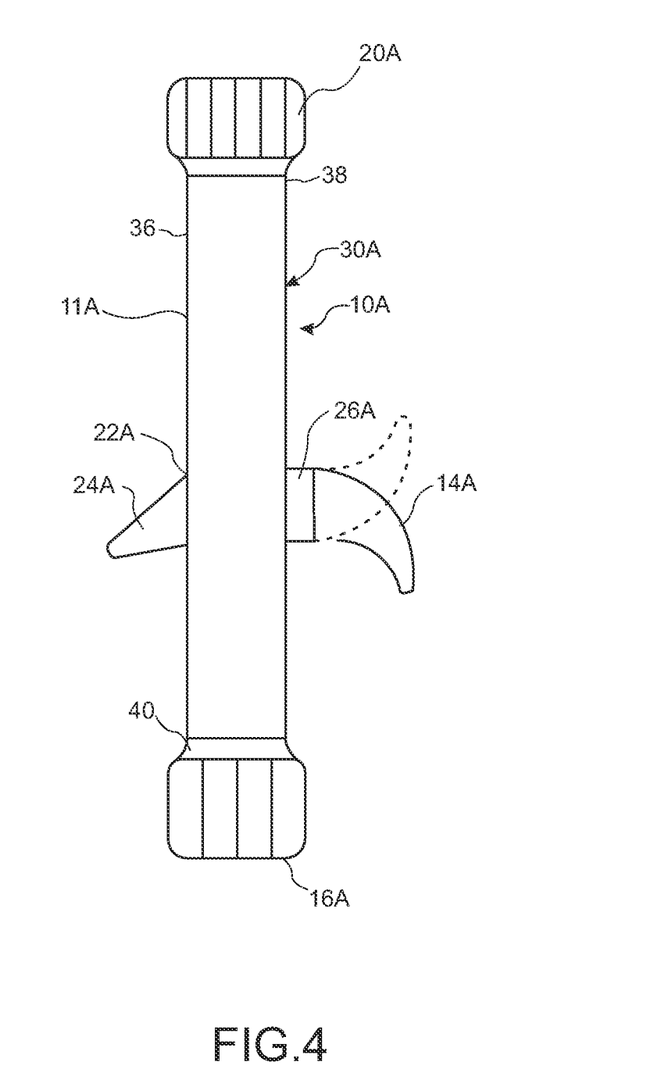
FIG. 4 is a plan view of an alternate adaptor that is constructed in accordance with an alternate embodiment of the present invention.
Figure 5:
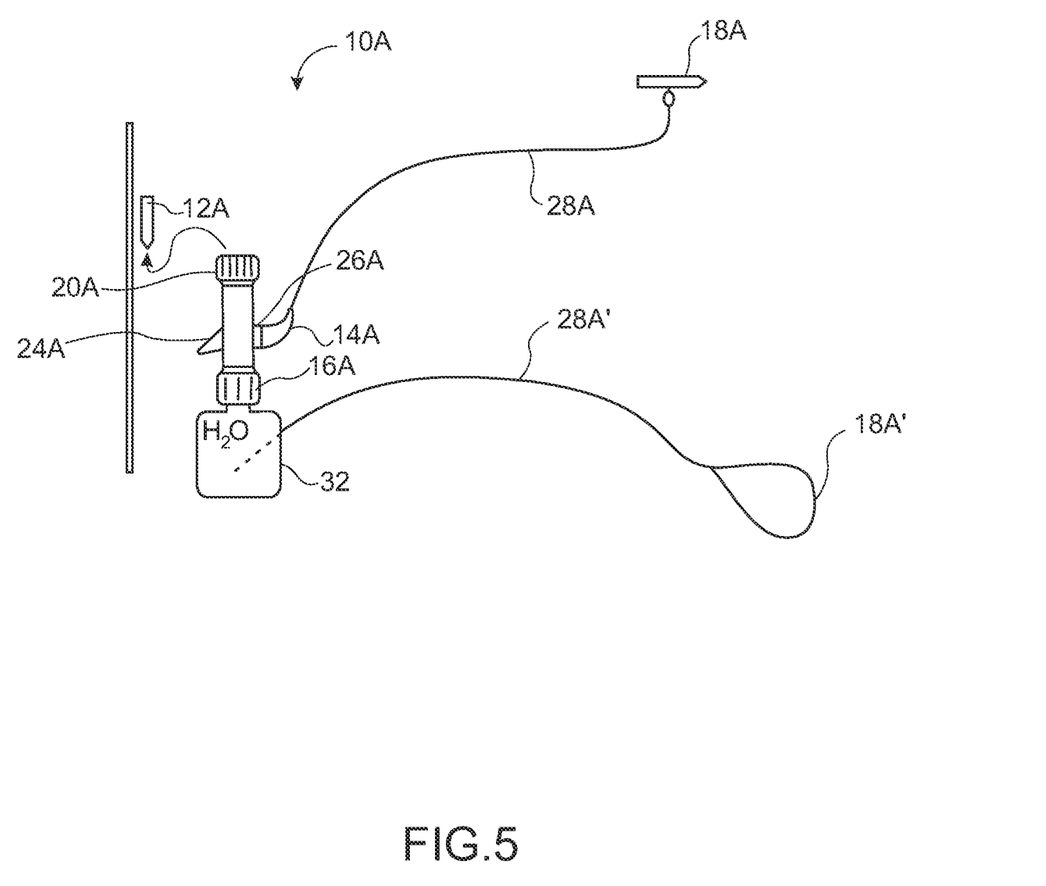
FIG. 5 is the alternate adaptor of FIG. 4 shown in use in a typical hospital setting.

Referring now to FIGS. 4 and 5, there is illustrated an alternate adaptor 10A, having an exterior surface 11A, for connecting an alternate pressurized gas supply 12A to two different alternate outlets 14A and 16A, with each alternate outlet 14A and 16A connected to a different gas delivery device 18A and 18A'. The alternate adaptor 10A of FIGS. 4 and 5 is generally designed for hospital or institutional use.

The alternate adaptor 10A is provided with an alternate receiving inlet 20A that connects to an alternate pressurized gas supply 12A such as the flowmeter shown in FIG. 5. The alternate adaptor 10A is hollow to allow gas to flow through it to at least two alternate outlets 14A and 16A. Positioned within the alternate adaptor 10A is an alternate valve 22A that is movable to various positions by an alternate switch 24A provided on the exterior of the alternate adaptor 10A so that it can be operated by a user. The user is normally a nurse or other caregiver when the alternate adaptor 10A is used in a hospital or institutional setting. The alternate valve 22A can be moved via the alternate switch 24A to allow gas to flow from the alternate gas supply 12A to a first alternate outlet 14A, to a second alternate outlet 16A, or to both the first and the second alternate outlets 14A and 16A provided on the alternate adaptor 10A.

Optionally, associated with one or more of the alternate outlets 14A and 16A, the alternate adaptor 10A may be provided with an alternate swivel mechanism 26A that functions to allow those alternate outlets 14A and 16A that are equipped with the alternate swivel mechanism 26A to swivel, thereby preventing tubing 28A and 28A' which is attached to the alternate outlets 14A and 16A from becoming twisted, tangled, or pinched.

FIG. 5 shows the alternate adaptor 10A in a typical hospital or institutional installation where the first alternate outlet 14A is connected via first alternate tubing 28A to a nebulizer 18A and where the second alternate outlet 16A is connected via second alternate tubing 28A' to a bubbler 32 that in turn supplies gas to a nasal cannula 18A'. This arrangement illustrates only one alternative swivel mechanism 26A associated with first alternate outlet 14A and no swivel associated with second alternate outlet 16A. Although not specifically illustrated, it is understood that either or both alternate outlets 14A and 16A may be provided with alternate swivel mechanisms 26A.

Although the nebulizer 18A, the bubbler 32 and the nasal cannula 18A' are illustrated in FIG. 5 as the gas delivery devices, any of a variety of gas delivery devices could alternately be attached to the first and second alternate outlets 14A and 16A.

Figure 6:
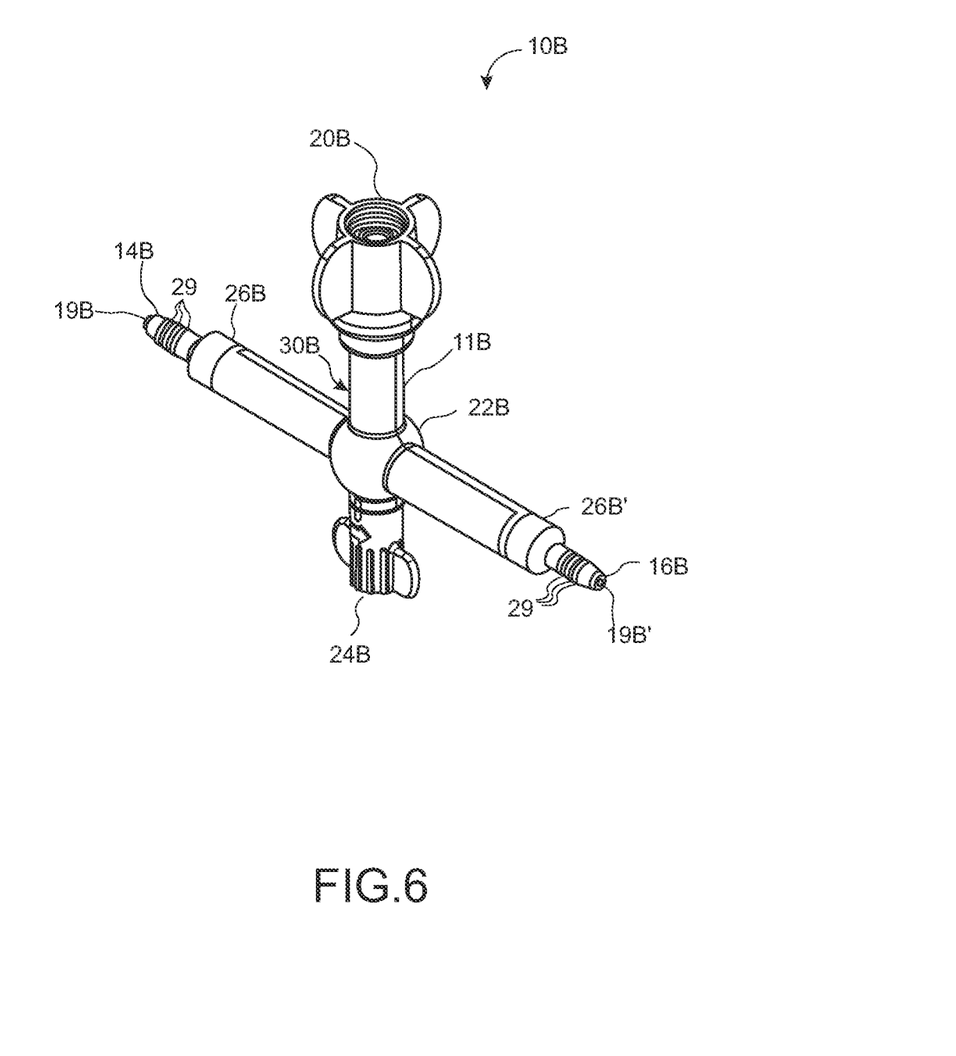
FIG. 6 is a perspective view of an alternative embodiment of an adaptor of the present invention.
Figure 7:
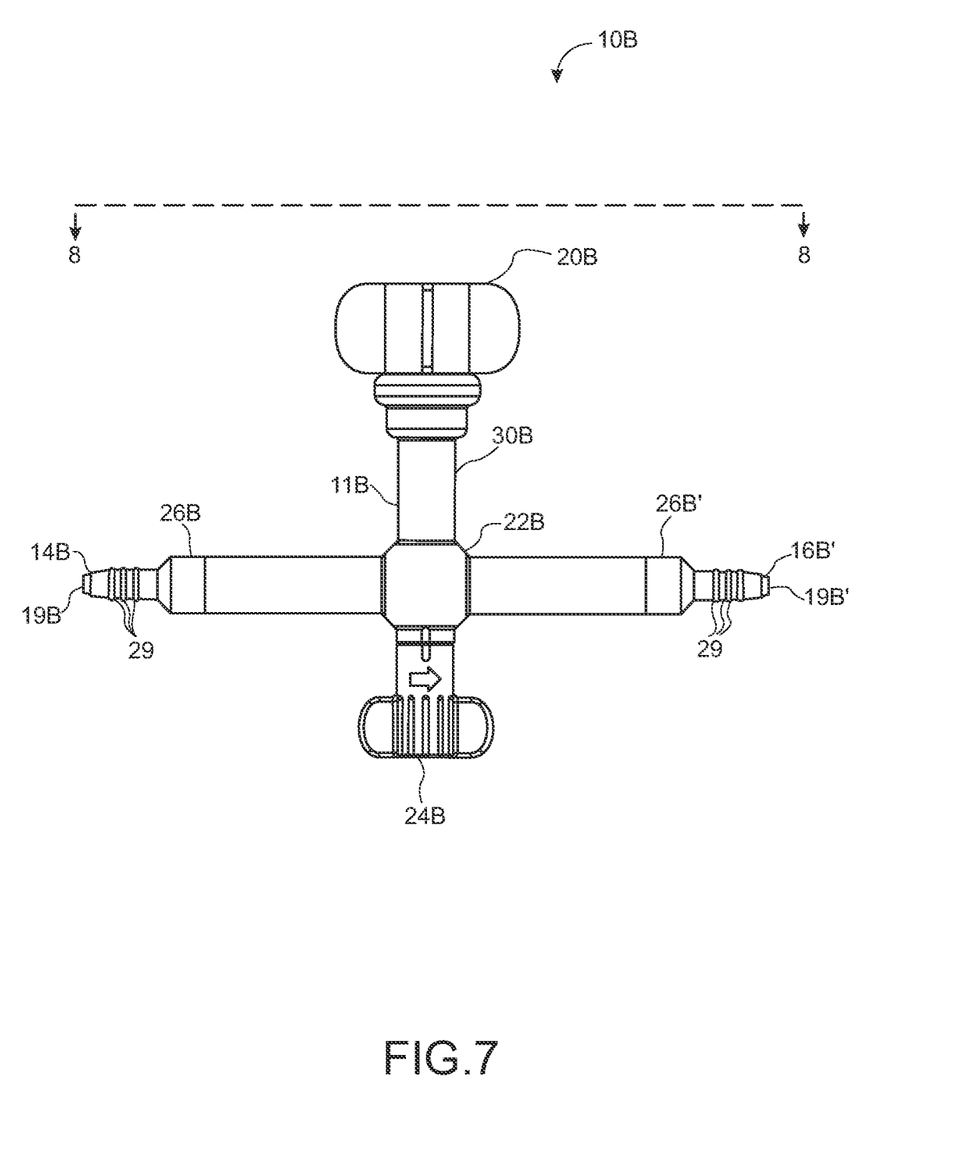
FIG. 7 is a plan view of the adaptor of FIG. 6.
Figure 8:
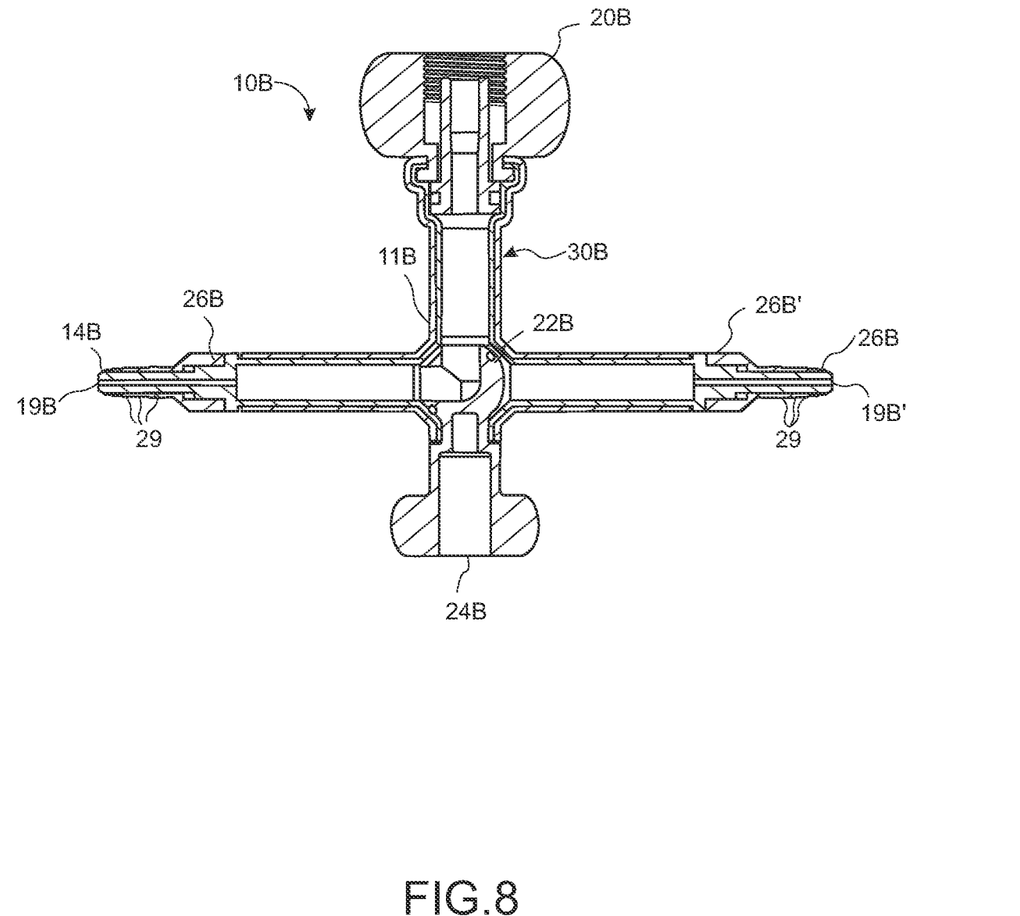
FIG. 8 is a cross-sectional view of the adaptor of FIG. 7 taken along line 8-8.

Turning now to FIGS. 6 through 8, there is shown therein an additional embodiment of the present invention, adaptor 10B. Adaptor 10B may comprise two different outlets 14B and 16B, with each outlet 14B and 16B connectable to a different gas delivery device, not shown, such as a nasal cannula, a c-pap machine, a bi-pap machine, a bubbler, or a nebulizer.

The adaptor 10B is provided with a receiving inlet 20B that connects to a pressurized gas supply 12, as illustrated in FIG. 1. The adaptor 10B is hollow to allow gas to flow therethrough to the outlets 14B and 16B. Positioned within the adaptor 10B is a valve 22B that is movable to various positions by a toggle, spigot or switch 24B provided on the exterior of the adaptor 10B so that it can be operated by a user. As shown in FIG. 8, the valve 22B may be moved via the switch 24B to allow gas to flow from the gas supply 12 to the first outlet 14B, to the second outlet 16B, or simultaneously to both the first and the second outlets 14B and 16B provided on the adaptor 10B.

The outlets 14B and 16B may be curved and/or tapered toward the openings 19B and 19B' in each outlet in order to securely receive, fit and/or connect tubing 28 and 28'. Associated with each of the outlets 14B and 16B, the adaptor 10 is provided with a separate swivel mechanism 26B and 26B' that function to allow the outlets 14B and 16B to swivel, thereby preventing tubing, not shown, when connected to outlets 14B and 16B, respectively, from becoming twisted, tangled, or pinched. The outlets 14B and 16B each may further comprise ridges or nubs 29 to engagingly grip tubing inserted over outlets 14B and 16B.

The adaptor 10, 10A and 10B may be any shape. By way of example, and as shown in FIGS. 1-3, the first outlet 14 and the second outlet 16 may be positioned so as to be axially aligned on the body 30A of the adaptor 10. The adaptor 10 may form first arm 32 and second arm 34 positioned to be perpendicular with respect to each other, wherein the first outlet 14 and the second outlet 16 may be axially aligned on the arm first 32. The first and second arms 32 and 34, each have a length and a diameter and the length of each of the arms ranges from about 38 mm to about 51 mm and the diameter of the arms ranges from about 7 mm to about 12 mm.

As shown in FIGS. 4-5, the adaptor 10A may form a substantially cylindrical hollow body 36 having a first end 38 and a second end 40. The first end 38 of the body 36 of the adaptor 10A terminates in the receiving outlet 20A, and the second end 40 terminates in the second outlet 16A. The first outlet 14A may be positioned in between the receiving inlet 20A and the second outlet 16A of the body 36 of adaptor 10A. The body 36 of the adaptor 10A has a diameter ranging from about 10 mm to about 30 mm.

While the invention has been described with a certain degree of particularity, it is manifest that many changes may be made in the details of construction and the arrangement of components without departing from the spirit and scope of this disclosure. It is understood that the invention is not limited to the embodiments set forth herein for the purposes of exemplification, but is to be limited only by the scope of the attached claim or claims, including the full range of equivalency to which each element thereof is entitled.

We claim:

1. An adaptor for connecting a pressurized gas supply, the adaptor having an exterior and comprising:
    a hollow body, wherein the hollow body has a receiving inlet, for connecting the adaptor to a pressurized gas supply, and a first outlet and a second outlet each adapted to connect to one or more gas delivery devices;
    a valve moveably positioned within the hollow body to control the flow of gas in the adaptor, wherein the valve is moveable to allow gas to flow from the gas supply to each of the first outlet, the second outlet, or simultaneously to both the first outlet and the second outlet;
    a first swivel mechanism in communication with the first outlet and a second swivel mechanism in communication with the second outlet, the first and second swivel mechanisms adapted to enable the first and second outlets to swivel and prevent entanglement, twisting or pinching of the gas delivery devices; and
    a switch provided on the exterior of the adaptor in communication with the valve, wherein the valve is operated by movement of the switch.

2. The adaptor of claim 1 wherein the adaptor is connectable to gas delivery devices via the first outlet and the second outlet and the gas delivery devices are selected from the group consisting of nasal cannulas, c-pap machines, bi-pap machines, bubblers, and nebulizers.

3. The adaptor of claim 1 wherein the second outlet further comprises a tube terminating in a swivel, wherein the tube is adapted for connection to a humidifier chamber.

4. The adaptor of claim 1 wherein the first outlet and the second outlet are positioned to be axially aligned on the body of the adaptor.

5. The adaptor of claim 1 wherein the first outlet and the second outlet are positioned to be perpendicular with respect to each other.

6. The adaptor of claim 1 wherein the hollow body forms a first end terminating in the receiving inlet, wherein the body has a diameter and wherein the diameter of the body ranges from about 10 to about 30 mm.

7. The adaptor of claim 1 wherein the hollow body forms a first arm terminating at one end in the first outlet and a second arm terminating at the other end in the second outlet, wherein the first and second arms each have a length and a diameter and wherein the length of each of the arms ranges from about 38 to about 51 mm and the diameter of the arms ranges from about 7 mm to about 12 mm.

8. The adaptor of claim 1 further comprising comprise ridges or nubs to engagingly grip tubing from the gas deliver devices that may be inserted over the first and second outlets.

9. The adaptor of claim 1 wherein the hollow body forms an elongate hollow tube having a first end and a second end, wherein the first end of the hollow tube terminates in a receiving outlet and wherein the second end of the hollow tube terminates in the second outlet.

10. The adaptor of claim 9 wherein the first outlet is positioned in between the first end and the second end of the hollow tube and terminates proximate the exterior or the hollow tube.

11. The adaptor of claim 9 wherein the hollow tube has a diameter ranging from about 10 mm to about 20 mm.

12. The adaptor of claim 9 wherein the receiving inlet has a diameter ranging from about 25 to about 30 mm.

13. The adaptor of claim 9 wherein the second outlet has a diameter ranging from about 25 to about 30 mm.

* * * * *